United States Patent
Utsugida

(10) Patent No.: US 10,183,107 B2
(45) Date of Patent: Jan. 22, 2019

(54) TUBE CLAMP FOR EXTRACORPOREAL CIRCULATOR AND EXTRACORPOREAL CIRCULATION SYSTEM

(71) Applicant: Terumo Kabushiki Kaisha, Tokyo (JP)

(72) Inventor: Tomoki Utsugida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 428 days.

(21) Appl. No.: 15/162,773

(22) Filed: May 24, 2016

(65) Prior Publication Data

US 2016/0361484 A1 Dec. 15, 2016

Related U.S. Application Data

(63) Continuation of application No. PCT/JP2014/083005, filed on Dec. 12, 2014.

(30) Foreign Application Priority Data

Feb. 7, 2014 (JP) .................................. 2014-022464

(51) Int. Cl.
*A61M 1/16* (2006.01)
*A61M 39/28* (2006.01)
*A61M 1/36* (2006.01)

(52) U.S. Cl.
CPC .......... *A61M 1/1698* (2013.01); *A61M 1/367* (2013.01); *A61M 1/3626* (2013.01);
(Continued)

(58) Field of Classification Search
CPC .. A61M 1/1698; A61M 1/3626; A61M 1/367; A61M 39/28; A61M 39/281;
(Continued)

(56) References Cited

U.S. PATENT DOCUMENTS

| 5,039,279 A | 8/1991 | Natwick et al. |
| 5,437,635 A * | 8/1995 | Fields ............... A61M 5/16813 604/65 |
| 2002/0085952 A1* | 7/2002 | Ellingboe ........... A61M 1/3621 422/45 |

FOREIGN PATENT DOCUMENTS

| CH | 604741 A | 9/1978 |
| DE | 19900320 C1 | 7/2000 |

(Continued)

OTHER PUBLICATIONS

European Search and Opinion Report, PCT/JP2014083005, dated Nov. 28, 2017.

*Primary Examiner* — Philip R Wiest
(74) *Attorney, Agent, or Firm* — MacMillan, Sobanski & Todd, LLC

(57) ABSTRACT

A tube clamp for an extracorporeal circulator recognizes various abnormal situations of the tube clamp and notifies a user. The tube clamp has a lid sensor, a tube sensor, and a plunger sensor. In a case where any one of detection of the closure of a lid portion via the lid sensor, detection of the mounting of a tube via the tube sensor, and detection of the movement of a plunger via the plunger sensor is not obtained despite the fact that there is an instruction for blocking the tube, it is determined that the blocking is abnormal. In a case where the three states including the closed state, the mounting state, and the movement state are detected despite the fact that there is no instruction for blocking the tube, it is determined that the tube is erroneously blocked. Such abnormal situations are notified to a user via an alarm.

8 Claims, 11 Drawing Sheets

(52) U.S. Cl.
CPC .......... *A61M 39/28* (2013.01); *A61M 39/281* (2013.01); *A61M 2205/14* (2013.01); *A61M 2205/18* (2013.01); *A61M 2205/3306* (2013.01); *A61M 2205/3334* (2013.01); *A61M 2205/502* (2013.01)

(58) Field of Classification Search
CPC .......... A61M 2205/14; A61M 2205/18; A61M 2205/3306; A61M 2205/3334; A61M 2205/502
See application file for complete search history.

(56) References Cited

FOREIGN PATENT DOCUMENTS

| | | |
|---|---|---|
| EP | 1535637 A1 | 6/2005 |
| JP | 2647124 B2 | 8/1997 |
| JP | 3061457 U | 9/1999 |
| JP | 2008253675 A | 10/2008 |
| JP | 4935433 B2 | 5/2012 |
| JP | 5439138 B2 | 3/2014 |

* cited by examiner

TUBE CLAMP FOR EXTRACORPOREAL CIRCULATOR AND EXTRACORPOREAL CIRCULATION SYSTEM

CROSS REFERENCE TO RELATED APPLICATIONS

This application is a continuation of PCT Application No. PCT/JP2014/083005, filed Dec. 12, 2014, based on and claiming priority to Japanese application no. 2014-022464, filed Feb. 7, 2014, both of which are incorporated herein by reference in their entirety.

TECHNICAL FIELD

The present invention relates to a tube clamp for an extracorporeal circulator, which transfers blood out of the body of a patient and circulates the blood, so as to block a tube through which the blood is transferred, and to an extracorporeal circulator using a tube clamp.

For example, in a case where a cardiac surgery operation is performed on a patient, extracorporeal blood circulation is performed in which after blood is drained from a vein (vena cava) of the patient by operating a pump of an extracorporeal circulator, and blood gas exchange is performed by an oxygenator, the blood is returned to an artery (aorta) of the patient again.

In a case where bubbles occur in blood flowing through a blood tube, or blood flows backwards, the patient may be put in danger. Accordingly, it is necessary to stop the flow of the blood momentarily, or to discharge the bubbles by directing blood to a separate route.

In a technique of stopping the flow of blood momentarily, for example, a control unit outputs a blocking instruction to a tube clamp, based on detection of bubbles in the blood tube performed by a bubble detecting sensor, such that the blood tube is blocked.

In a technique of discharging bubbles via a separate route, for example, as illustrated in Japanese patent 4935433B2, a blood filter 19 is provided on a blood circuit, and bubbles caused by a pressure loss are discharged via the separate route.

Technical Problem

In the technique disclosed in Japanese patent 4935433B2 in which a bubble discharge route is separately provided, the size of an apparatus may be increased, the length of installation time may be increased, and thrombi formation may be highly likely to occur. Particularly, in a case where assistance for circulation is urgently required, an increase in the length of installation time becomes a great obstacle in the emergency medical care field. Needless to say, an increase in the possibility of the occurrence of thrombi formation may adversely affect the prognosis of the patient.

In contrast, in a technique of blocking a tube with a tube clamp, such a problem is unlikely to occur. Even if the tube clamp is used, however, an unfavorable situation for a patient can conceivably occur. For example, even if the tube clamp receives a blocking instruction from the control unit, set-up or installation of the tube clamp may be improperly done due to a human error, or the tube clamp may be erroneously operated, and thus, blocking by the tube clamp might not be well achieved. Alternatively, there is a problem in that the tube clamp may become inadvertently blocked, despite the fact that the control unit does not output a blocking instruction. In a case where the tube is erroneously blocked in such unfavorable situations, if proper measures are not quickly performed, the patient may be put in great danger, which is a problem.

An object of the present invention is to provide a tube clamp for an extracorporeal circulator in which a user can properly recognize various abnormal situations of the tube clamp in a technique of blocking a tube with the tube clamp, and an extracorporeal circulator therefor.

SUMMARY OF THE INVENTION

According to the present invention, in order to solve the problem, there is provided a tube clamp for an extracorporeal circulator that is used in the extracorporeal circulation system which transfers blood out of a body of a patient and circulates the blood via the tube, and that blocks the tube based on a blocking instruction in response to an occurrence of bubbles in the blood and/or backflow of the blood occurring in the tube, wherein the tube clamp including; a body portion including a mounting space or passageway in which the tube is mounted; a lid portion that closes the mounting space; a plunger that presses and blocks the tube; and a clamp sensing means (i.e., a sensor assembly) that detects a mounting state in which the tube is mounted in the mounting space. The tube clamp has a closed state in which the mounting space is closed by the lid portion, and a movement state in which the plunger is moved.

In this configuration, the tube clamp includes the body portion including the mounting space in which the tube is mounted; the lid portion that closes the mounting space; and the plunger that presses and blocks the tube. Accordingly, the tube clamp blocks the tube based on three conditions such as "the tube being mounted", "the lid portion being closed", and "the plunger being moved".

In this configuration, the sensing means responds to the three conditions, while characteristics of the tube clamp are also taken into consideration. As a result, it is possible to precisely check the state of each portion, and a user can recognize various erroneous operations or incorrect operations of the tube clamp. For example, in a case where the mounting of the tube is detected, the closure of the lid portion is detected, the movement of the plunger is detected, that is, all of three states are detected, it means that the tube becomes correctly blocked. In contrast, in a case where the three states are detected, despite the fact that a blocking instruction is not output, it means that the tube is erroneously blocked. In a case where a blocking instruction is not output and the closure of the lid cannot be detected, it means that the tube is not erroneously blocked, but preparation for use has not been completed.

In the extracorporeal circulator using the tube clamp with the aforementioned configuration, the blood circuit is preferably provided with notification means which notifies a user that the tube is not blocked even though there is the blocking instruction and sensor assembly is failing to detect any one of the closed state, the mounting state, and the movement state.

Since the extracorporeal circulator includes the tube clamp as described herein, it is possible to obtain the aforementioned effects, and to notify the user that the tube is not correctly blocked despite the fact that there is the blocking instruction, via the notification means. Accordingly, since the user can ascertain that the tube, which is intended to be blocked, but is not blocked, the user can quickly take measures corresponding to a specific situation by performing an emergency treatment such as contracting the tube with forceps, or by inspecting whether bubbles enter a patient.

In the extracorporeal circulator using the tube clamp with the aforementioned configuration, the blood circuit is preferably provided with notification means which notifies a user that the tube clamp erroneously blocks the tube even though there is no blocking instruction if the sensing means is detecting the closed state, the mounting state, and the movement state.

In this configuration, since the extracorporeal circulator includes the tube clamp as described herein, it is possible to obtain the aforementioned effects, and to notify the user that the tube is erroneously blocked despite the fact that there is no blocking instruction, via the notification means. Accordingly, for example, the user can quickly take specific measures so as to eliminate an unnecessary blocked state by moving a plunger of the tube clamp away from the tube.

In the extracorporeal circulator using the tube clamp with the aforementioned configuration, the blood circuit is preferably provided with notification means which notifies a user that preparation for use of the tube clamp has not been completed, if there is no blocking instruction and if the clamp sensing means does not detect the closed state and/or the mounting state.

In this configuration, it is possible to obtain the aforementioned effects, and to notify the user that the preparation of the tube clamp has not been completed, via the notification means. Accordingly, the user can take specific measures for completing the preparation by dealing with the incomplete preparations, for example, mounting the tube on the tube clamp, and prevent the occurrence of a state in which the tube cannot be blocked when necessary.

The tube clamp is preferably provided with display means which notifies the user that preparation for closing the tube has been completed, if the sensing means does not detect the movement state, and detects the closed state and the mounting state.

Accordingly, the user can easily confirm completion of the preparation for use of the tube clamp by observing the nearby display means (for example, a lamp) when the user prepares to use the tube clamp.

The blood circuit is preferably provided with a flow rate detecting sensor that detects a blood flow rate in the tube. The notification means preferably notifies the user that the tube clamp correctly blocks the tube, if the sensing means detects the closed state, the mounting state, and the movement state and if the flow rate detecting sensor substantially does not detect the blood flow rate.

After it is confirmed that the tube clamp blocks the tube by detecting the three states including "the closure of the lid portion", "the mounting of the tube", and "the movement of the plunger", and substantially no blood flow rate is finally confirmed, the user is notified that the tube is blocked. Accordingly, even if the sensing means fails, accurate notification can be sent.

The "substantially no detection of the blood flow rate" implies that "there is no detection of a flow rate exceeding the flow rate of blood which still flows through the tube, even if the tube is properly blocked". That is, even if a motor on the blood circuit is stopped concurrently with the blocking of the tube, a small amount of blood may flow through the tube due to other factors such as gravity, and such a small amount of flow rate is not taken into consideration.

More preferably, the extracorporeal circulator is configured such that the aforementioned various configurations of the notification means are properly combined together, and thus, it is possible to notify the user of the delicate state of the tube clamp, and the user can quickly take more proper measures.

Advantageous Effects of Invention

According to the present invention, it is possible to provide a tube clamp for an extracorporeal circulator in which a user can properly recognize various abnormal situations of the tube clamp in an extracorporeal circulation system.

DESCRIPTION OF PREFERRED EMBODIMENTS

Hereinafter, preferable embodiments of the present invention will be described in detail with reference to the accompanying drawings. The embodiments which will be described below are preferred specific examples of the present invention, and thus, the embodiments are accompanied by various preferable technical limitations. It is noted that the scope of the present invention is not limited to the embodiments unless the following description explicitly limits the invention.

"Extracorporeal circulation" performed by an extracorporeal circulation system includes an "extracorporeal circulation operation" and a "supplementary circulation operation". The "extracorporeal circulation operation" implies that a blood circulation operation is performed by the extracorporeal circulator, and a blood gas exchange operation (e.g., addition of oxygenation and/or removal of carbon dioxide) is performed while blood circulation by the heart of a patient is temporarily stopped during surgery. The "supplementary circulation operation" implies that a blood circulation operation is assisted by the extracorporeal circulator in a case where the heart of the patient does not fully function, or gas exchange is insufficiently performed by the lung. An apparatus for supplementary circulation may also have a function of performing a blood gas exchange operation.

[Schematic Configuration of Extracorporeal Circulator]

Figure 1:
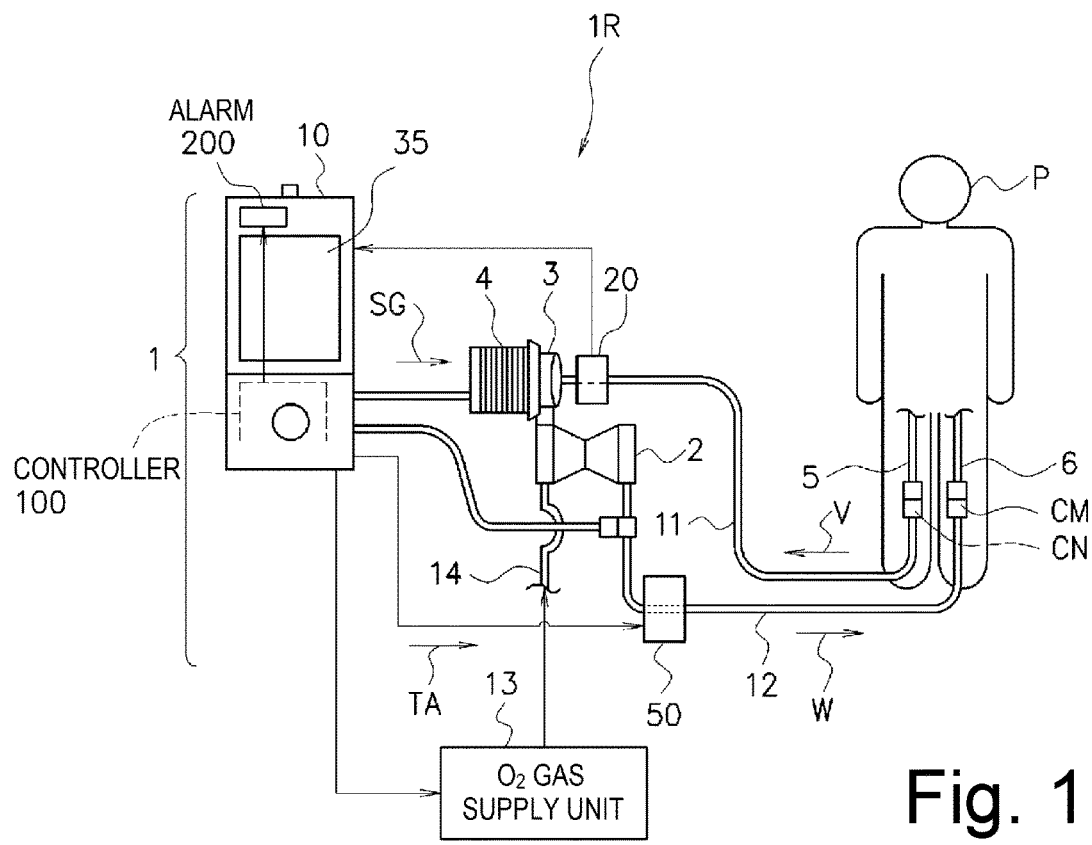
FIG. 1 is a system diagram illustrating a preferable embodiment of an extracorporeal circulator of the present invention.

Initially, the schematic configuration of the extracorporeal circulator of the embodiment will be described with reference to FIG. 1. FIG. 1 is a system diagram illustrating a preferable embodiment of the extracorporeal circulator of the present invention.

A extracorporeal circulator 1 in this drawing has a blood circuit (also referred to as a "blood circulation circuit") 1R through which blood drained from a vein of a patient P is returned to an artery of the patient again. The blood circuit 1R are provided with an oxygenator 2 that performs a blood gas exchange operation; a centrifugal pump 3 that transfers blood; a drive motor 4 which is a drive source of the centrifugal pump 3; a vein catheter (blood removal catheter) 5; an artery catheter (blood transfer catheter) 6; and a controller 10 that controls various components provided in the blood circuit 1R. These components substitute for or supplement the heart and the lung.

The vein catheter 5 is inserted through a femoral vein, and a tip of the vein catheter 5 is emplaced in the right atrium. The artery catheter 6 is inserted through a femoral vein. The vein catheter 5 is connected to the centrifugal pump 3 via a blood drainage tube 11. The blood drainage tube (also referred to as a blood removal line) 11 is a tube line through which blood is transferred.

When the drive motor 4 operates to a command SG from the controller 10, the centrifugal pump 3 drains blood from the blood drainage tube 11. After the drained blood passes through the oxygenator 2, the drained blood can be returned to the patient P through a blood transfer tube (also referred to as a blood transfer line) 12.

The blood drainage tube 11 and the blood transfer tube 12 can be formed of tube lines which are made of synthetic resin such as vinyl chloride resin or silicone rubber, and are highly transparent and flexible. Particularly, the blood transfer tube 12 has flexibility and a desired outer diameter such that the blood transfer tube 12 can be squeezed by a plunger 85 (to be described later) (refer to FIG. 5). Blood flows through the blood drainage tube 11 in a V direction, and flows through the blood transfer tube 12 in a W direction.

The oxygenator 2 is disposed between the centrifugal pump 3 and the blood transfer tube 12. The oxygenator 2 is a membrane oxygenator, and a hollow fiber membrane oxygenator is preferably used as the oxygenator 2. Oxygen gas is supplied to the oxygenator 2 from an oxygen gas supply unit 13 via a tube 14.

The controller 10 includes a control unit 100 that controls components such as the drive motor 4, a bubble detecting sensor 20 (to be described later), and a tube clamp 50 (to be described later). The controller 10 includes an alarm 200 as notification means such as a buzzer or a speaker, and the alarm 200 is sounded at detection of an abnormality. The controller 10 includes a display screen 35, and the display screen 35 displays information regarding various settings such as the setting of the rotational speed of the drive motor 4 and the linkage setting of the tube clamp 50. The bubble detecting sensor 20 and the tube clamp 50 are provided as safety devices on the blood circuit 1R.

The bubble detecting sensor 20 is a detector that detects bubbles present in blood. The bubble detecting sensor 20 is preferably disposed in the middle of the blood drainage tube 11.

A well-known ultrasonic detection sensor can be used as the bubble detecting sensor 20. Since bubbles present in blood flowing through the blood drainage tube 11 change a received intensity of transmitted ultrasonic waves, the ultrasonic detection sensor can detecting the bubbles. The ultrasonic detection sensor also serves as a flow rate detecting sensor that transmits to and receives ultrasonic waves from blood in both of a blood flow direction and a backflow direction, and is capable of detecting a blood flow rate based on the difference between the transmission times of the ultrasonic waves in the directions (for this reason, hereinafter, the "bubble detecting sensor 20" is referred to as a "bubble flow rate detecting sensor 20").

The bubble flow rate detecting sensor 20 transmits a detected result indicating existence or absence of bubbles, and a detected result indicating the value of the blood flow rate to the control unit 100 of the controller 10. In a case where the value of a blood flow rate detected by the bubble flow rate detecting sensor 20 is negative, the control unit 100 determines that blood flows backwards.

The tube clamp 50 is a blocking device that blocks the flow path of the blood transfer tube 12 by pinching closed (i.e., squeezing) the blood transfer tube 12 according to an instruction from the control unit 100. In FIG. 1, the tube clamp 50 is disposed in the middle of the blood transfer tube 12, and is preferably disposed at least on the downstream side of the bubble flow rate detecting sensor 20. That is, if the bubble flow rate detecting sensor 20 disposed on the upstream side of the tube clamp 50 detects bubbles in the blood drainage tube 11 and if the control unit 100 receives a signal for the detection of the bubbles, the control unit 100 outputs a blocking instruction TA to the tube clamp 50, and the tube clamp 50 prevents undesirable transferring of the bubbles to the patient P by quickly blocking the blood transfer tube 12. In a case where the control unit 100 determines that blood flows backwards in the blood drainage tube 11, based on the detected result from the bubble flow rate detecting sensor 20 indicating the value of the blood flow rate, the tube clamp 50 quickly blocks the blood transfer tube 12 according to the blocking instruction TA from the control unit 100.

Hereinafter, the tube clamp will be described in detail.

Figure 2:
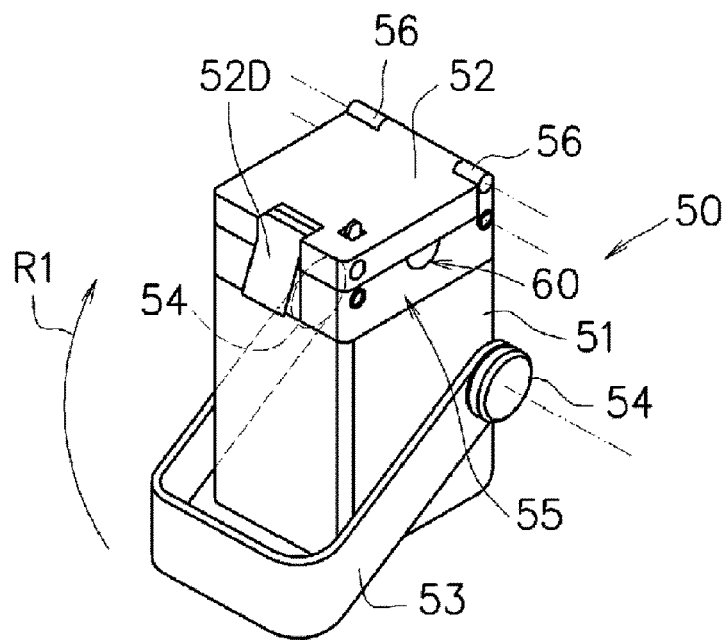
FIG. 2 is a perspective view illustrating an example of a preferable structure of a tube clamp.

FIG. 2 is a perspective view illustrating an example of a preferable structure of the tube clamp 50. As illustrated in FIG. 2, the tube clamp 50 includes a body portion 51 and a lid portion 52. The entire shape of the body portion 51 is rectangular parallelepiped, and the plunger 85 (refer to FIG. 5) is disposed inside the body portion 51, and is moved in a vertical direction. A substantially U-shaped operation lever 53 is mounted on the body portion 51 via a pair of mounting portions 54. The operation lever 53 is linked to the plunger 85 (refer to FIG. 5). The operation lever 53 is turned around the pair of mounting portions 54 to be lifted upwards in an R1 direction such that the plunger 85 (refer to FIG. 5) can be moved downwards. The lid portion 52 is an opening and closing lid that can be turned around a hinge portion 56, and is capable of opening and closing an upper portion 55 of the body portion 51. The lid portion 52 is a transparent member, the majority of which is formed of plastic except for the hinge portion 56 and a hook 52D (to be described later).

Even if the lid portion 52 is closed, a user can visually check the inside of the body portion 51 through the lid portion 52.

Figure 3:
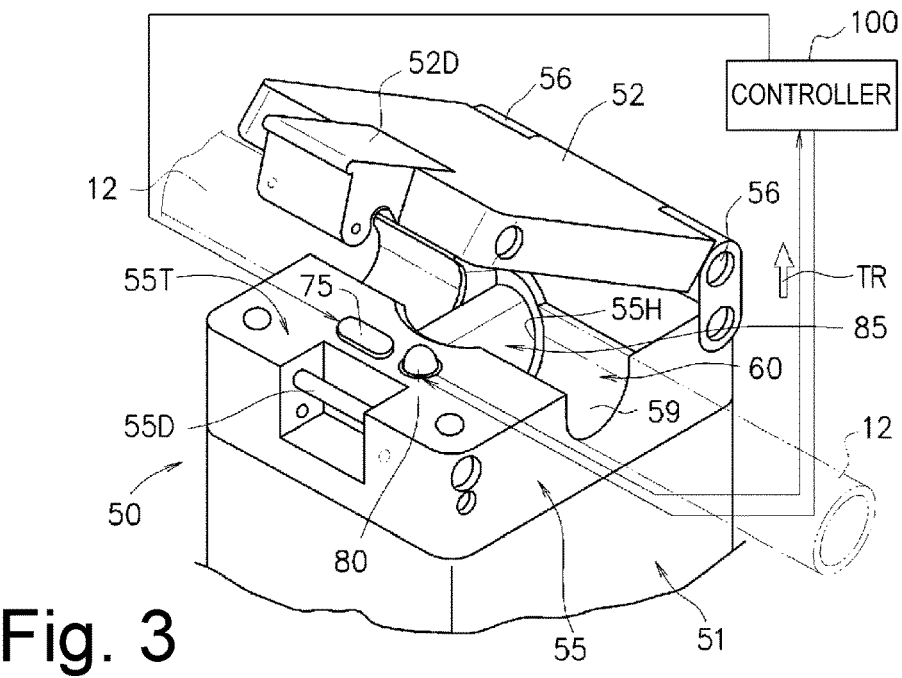
FIG. 3 is a perspective view illustrating an upper portion of the tube clamp illustrated in FIG. 2.
Figure 4A:
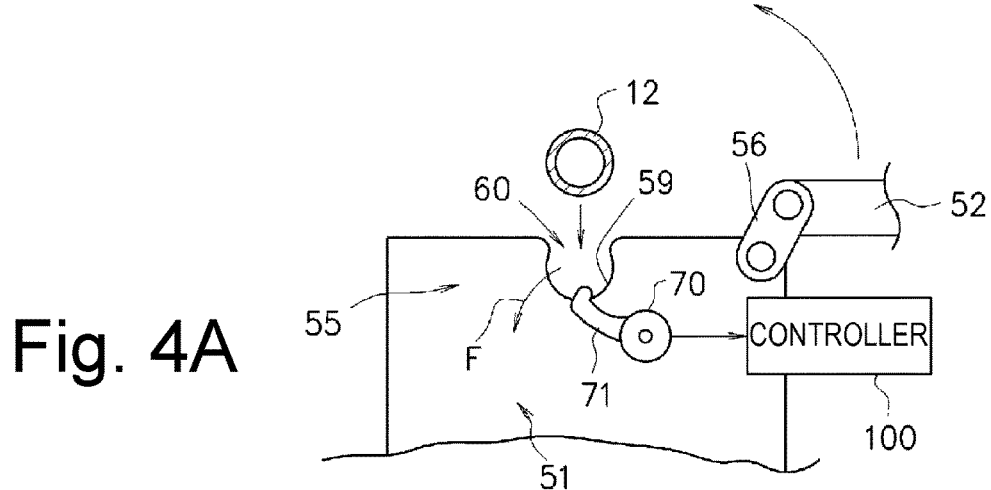
FIG. 4A and FIG. 4B are side views illustrating an upper portion of a body portion and a lid portion of the tube clamp illustrated in FIG. 2.
Figure 4B:
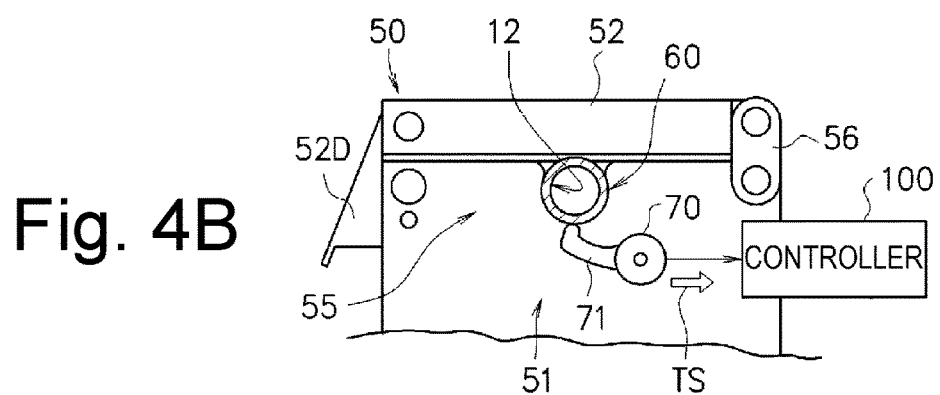

FIG. 3 is a perspective view illustrating an example of the structures of the upper portion 55 and the lid portion 52 of the tube clamp 50. FIG. 4 is a side view illustrating the upper portion 55 of the body portion 51 and the lid portion 52 of the tube clamp 50, wherein FIG. 4(A) illustrates an open state in which the lid portion 52 is open, and FIG. 4(B) illustrates a closed state in which the lid portion 52 is closed.

As illustrated in FIGS. 3 and 4, the upper portion 55 of the body portion 51 is provided with a tube setting portion 59 formed as a channel on which a portion of the blood transfer tube 12 is mounted along a horizontal direction. The tube setting portion 59 is a groove having a substantially arc-shaped section conforming to the exterior of the blood transfer tube 12. The blood transfer tube 12 is attachably and detachably fitted into the tube setting portion 59. A space above the tube setting portion 59 refers to a mounting space 60 providing a passageway in which the blood transfer tube 12 is mounted.

The mounting space 60 is bounded on the top by the lid portion 52. In the embodiment, the blood transfer tube 12 can be interposed between the tube setting portion 59 and the lid portion 52 by the closing of the lid portion 52 from a pre-insertion state where the blood transfer tube 12 is not yet installed as illustrated in FIG. 4(A) to an installed state in which the blood transfer tube 12 has been set as illustrated in FIG. 4(B).

As illustrated in FIG. 3, the lid portion 52 includes the hook 52D. When the hook 52D is engaged with a fastening member 55D of the upper portion 55 of the body portion 51, as illustrated in FIG. 4(B), a closure of the lid portion 52 is fixed such that the blood transfer tube 12 is positively retained within the passageway of the body portion 51.

Figure 5A:
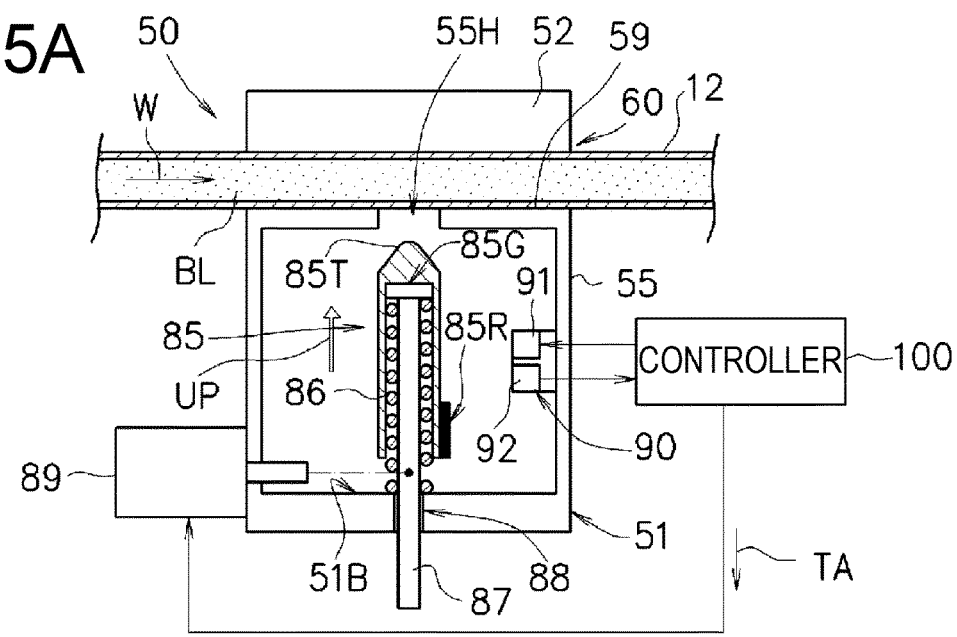
FIG. 5A is a longitudinal sectional view illustrating a state in which preparation for use of the tube clamp has been correctly completed.

As illustrated in FIG. 3, the tube setting portion 59 includes a through hole 55H that is formed along a width direction of (i.e., transverse to) the groove. The tube setting portion 59 is configured to enter and exit the through hole 55H such that the plunger 85 approaches and moves away from the lid portion 52. An example of the structure of the plunger 85 will be described with reference to FIG. 5. FIG. 5(A) illustrates a state in which the plunger 85 does not yet press the blood transfer tube 12 mounted in the mounting space 60 which has been installed in a normal state in which proper emplacement of the blood transfer tube 12 has been completed, and FIG. 5(B) illustrates a state in which the plunger 85 presses the blood transfer tube 12 against the lid portion 52, so that the blood transfer tube 12 becomes blocked by being pinched closed.

Figure 5B:
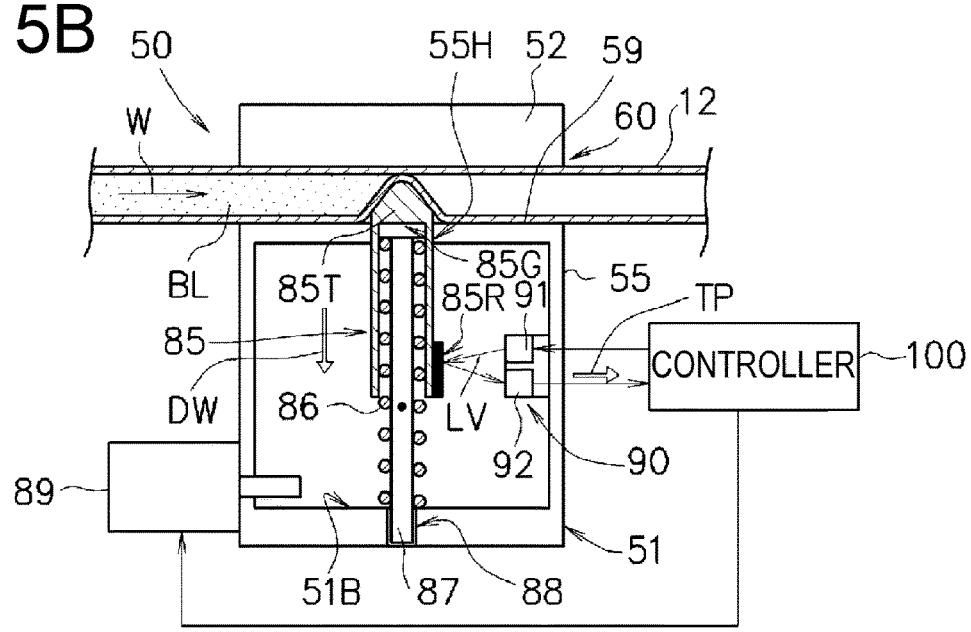
FIG. 5B is a longitudinal sectional view illustrating a state in which a tube is normally blocked based on a blocking instruction.

As illustrated in FIG. 5(B), the plunger 85 is a pressing member that closes the blood transfer tube 12 by pressing the blood transfer tube 12 against the lid portion 52 via a force of a spring 86, thereby collapsing and squeezing closed the inner space of the blood transfer tube 12. In FIG. 5, the entire shape of the plunger 85 is longitudinally cylindrical, and the spring 86 is accommodated thereinside. A shaft portion 87 is provided longitudinally inside the spring 86. An upper portion of the shaft portion 87 is connected to an inner tip portion 85G of the plunger 85, and a lower portion of the shaft portion 87 passes through a guide hole 88 formed in the body portion 51. A tip portion 85T of the plunger 85 has a peaked or tapered end section, and thus, the plunger 85 easily squeezes the blood transfer tube 12.

When the operation lever 53 illustrated in FIG. 2 is manually pushed upwards in the R1 direction, the plunger 85 is moved downwards in a DW direction (direction in which the plunger 85 moves away from the lid portion 52) from a state where the plunger 85 protrudes to the lid portion 52 from the through hole 55H of the tube setting portion 59 illustrated in FIG. 5(B), to the state illustrated in FIG. 5(A) wherein the plunger 85 is retracted to overcome the force of the spring 86. As a result, the preparation for use is completed. According to an instruction from the control unit 100, a solenoid 89 is locked to the plunger 85 including the shaft portion 87 via a structural portion (not illustrated) such that the retracted state of the plunger 85 illustrated in FIG. 5(A) is selectably achieved.

In a case where the bubble flow rate detecting sensor 20 detects bubbles in the blood transfer tube 12, or the backflow of blood, the control unit 100 outputs the blocking instruction TA to the solenoid 89, the retracted state of the plunger 85 including the shaft portion 87 illustrated in FIG. 5(A) is released, the plunger 85 is moved into the body portion 51 in an UP direction by the force of the spring 86, and as illustrated in FIG. 5(B), the plunger 85 squeezes the blood transfer tube 12 against the lid portion 52.

The tube clamp 50 is configured as described above, and as illustrated in FIG. 5(B), three states such as a "mounting state in which the blood transfer tube 12 is mounted in the mounting space 60", a "closed state in which the mounting space 60 is closed by the lid portion 52", and a "movement state in which the plunger 85 is moved to the lid portion 52" are obtained, and eventually, blocking is correctly performed.

In the present invention, a clamp sensing means (i.e., a clamp monitor comprised of a sensor assembly) is provided in the tube clamp 50 so as to be able to precisely check and detect the three states. In a preferred embodiment, the sensor assembly is formed of a tube sensor (a sensor for detecting emplacement of a tube), a lid sensor (a sensor for detecting a position of the lid), and a plunger sensor (a sensor for detecting a position of the plunger).

Firstly, a tube sensor 70 of the clamp sensing means will be described with reference to FIG. 4. The tube sensor 70 is a detector that detects the presence of (i.e., the correct mounting of) the blood transfer tube 12 mounted in the mounting space 60.

The tube sensor 70 includes a detection end portion 71 which is in contact with the blood transfer tube 12. The detection end portion 71 is provided in the vicinity of the tube setting portion 59 of the body portion 51, preferably, in a portion of an inner wall of the tube setting portion 59 close to the plunger 85 when the potential rupture (refer to FIG. 8) of the blood transfer tube 12 is taken into consideration. In a case where the detection end portion 71 is provided in a portion of the inner wall of the tube setting portion 59, the detection end portion 71 protrudes from the inner wall into the tube setting portion or channel 60.

When the blood transfer tube 12 is placed into the mounting space 60 such that a state where the blood transfer tube 12 is not yet mounted as illustrated in FIG. 4(A) is changed to a state where the blood transfer tube 12 has been mounted as illustrated in FIG. 4(B), the detection end portion 71 is pressed and turned in an F direction by the blood transfer tube 12. Accordingly, the tube sensor 70 transmits a tube mounting state signal TS to the control unit 100, and thus, the control unit 100 is capable of recognizing a mounting state in which the blood transfer tube 12 is either mounted in or absent from the mounting space 60.

Figure 6A:
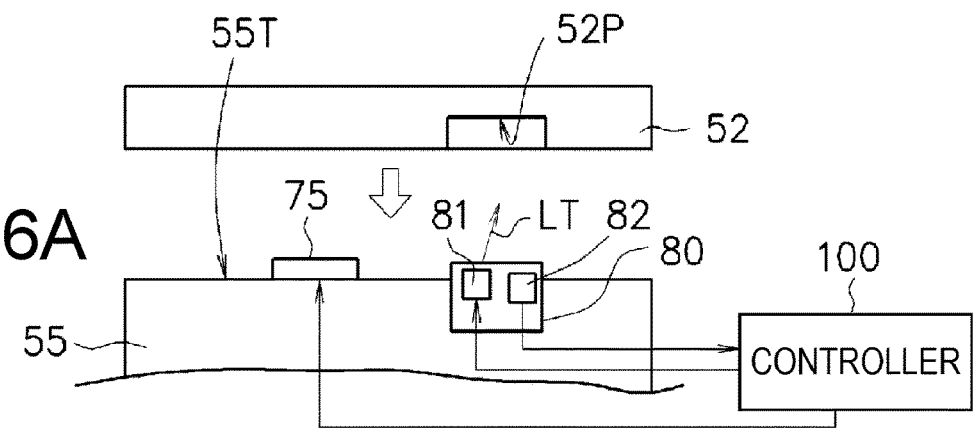
FIG. 6A and FIG. 6B are views illustrating display means provided on the upper of the body portion, and a lid sensor.

Hereinafter, a lid sensor 80 of the clamp sensing means will be described with reference to FIGS. 3 and 6. FIG. 6 is a view illustrating display means 75 provided on the upper portion 55 of the body portion 51 and the lid sensor 80, wherein FIG. 6(A) illustrates an open state in which the lid portion 52 is open, and FIG. 6(B) illustrates a closed state in which the lid portion 52 is closed (a display unit 80 will be described later).

Figure 6B:
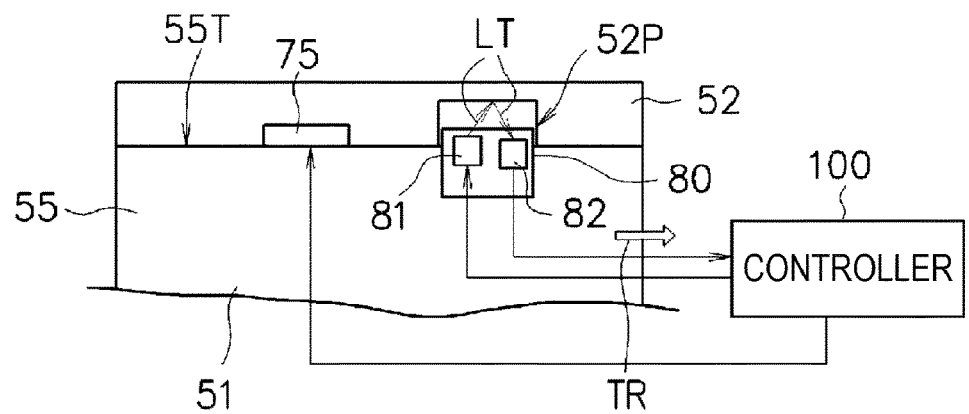

As illustrated in FIGS. 3 and 6, the lid sensor 80 is provided on an upper end surface portion 55T of the body portion 51. The lid sensor 80 is a detector that detects a closed state in which the mounting space 60 is closed by the lid portion 52. As illustrated in FIG. 6, the lid sensor 80 is a photo interrupter including a light emitting element 81 and a light receiving element 82. In a state where the lid portion 52 is closed as illustrated in FIG. 6(B), light LT from the light emitting element 81 is reflected by a reflective portion 52P of the lid portion 52, and is received by the light receiving element 82. Accordingly, the lid sensor 80 detects in a contactless manner the closed state in which the mounting space 60 is closed by the lid portion 52, and the lid sensor 80 transmits a closed state signal TR to the control unit 100 such that the control unit 100 is capable of recognizing the closure of the lid portion 52.

Hereinafter, the plunger sensor 90 of the sensing means will be described with reference to FIG. 5. An optical sensor can be used as the plunger sensor 90, and the plunger sensor 90 is a photo interrupter including a light emitting element 91 and a light receiving element 92. A reflective plate 85R is preferably provided on an outer circumferential side surface of the plunger 85. As illustrated in FIG. 5(B), in a case where the plunger 85 is moved upwards to the lid portion 52, and presses the blood transfer tube 12, light LV from the light emitting element 91 of the plunger sensor 90 is reflected from the reflective plate 85R, and is received by the light receiving element 92. Accordingly, a blocking signal TP, which indicates a blocked state in which the blood transfer tube 12 is pressed and blocked, is transmitted from the light receiving element 92 to the control unit 100 such that the control unit 100 is capable of recognizing the blocked state in which the blood transfer tube 12 is pressed and blocked by the plunger 85.

As illustrated in FIGS. 3 and 6, the display means 75 is provided in the tube clamp 50 including the clamp sensing means so as to notify a user of a complete preparation state after the preparation for use has been successfully completed.

The display means 75 may be a lamp, or a screen or the like on which a message is displayed. In the embodiment, the display means 75 is formed of a lamp (preferably, an LED), and in a case where the complete preparation state is normal as illustrated in FIG. 5(A), the display means 75 lights up green according to an instruction from the control unit 100. Specifically, in a state where the plunger sensor 90 does not detect a movement of the plunger 85, if the lid sensor 80 detects a closed state as illustrated in FIG. 6(B) and if the tube sensor 70 detects the mounting of the tube as illustrated in FIG. 4(B), the display unit 75 illustrated in FIGS. 3 and 6 lights up.

The display means 75 is disposed on the upper end surface portion 55T of the body portion 51 in order for a user to easily observe the display means 75 during preparation, and a light-up state can be observed through the transparent lid portion 52.

Hereinafter, for clear understanding of the present invention, examples of various abnormal states (abnormalities) of the tube clamp 50 will be described with reference to FIGS. 7 to 10 prior to describing an example of the operation of the extracorporeal circulator 1. Details of the structure illustrated in FIG. 5 are simplified in FIGS. 7 to 10.

Figure 7A:
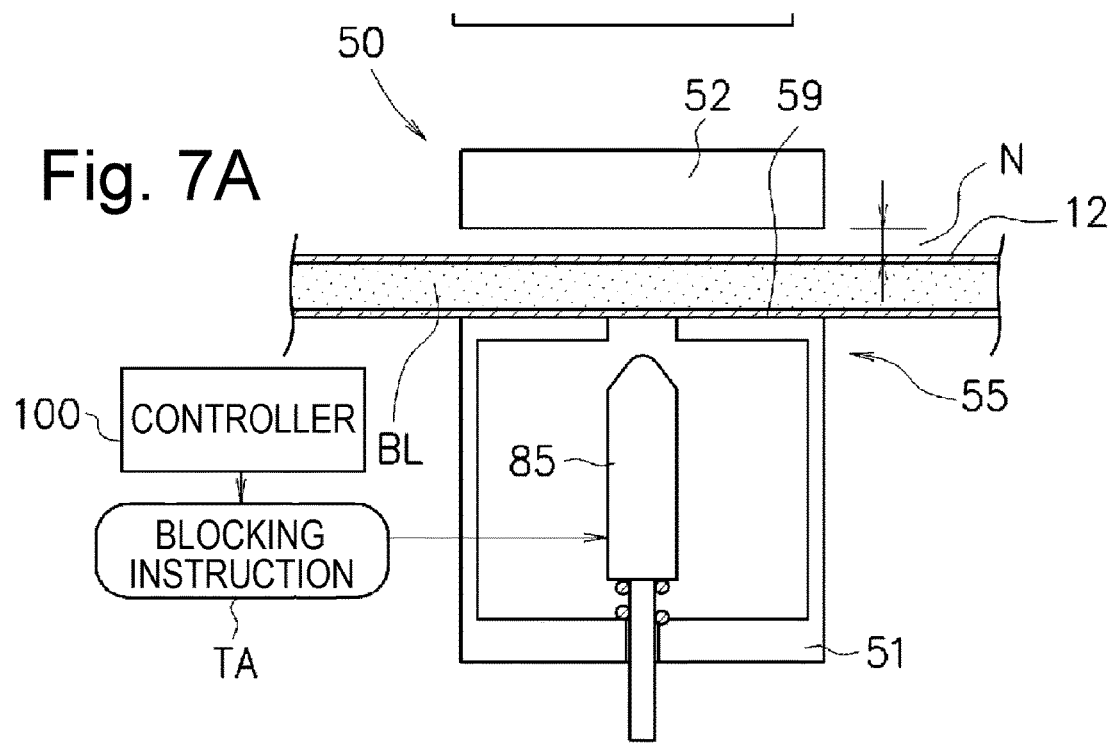
FIG. 7A and FIG. 7B are views illustrating abnormal clamping of a blood transfer tube in a case where the lid portion is insufficiently locked.
Figure 7B:
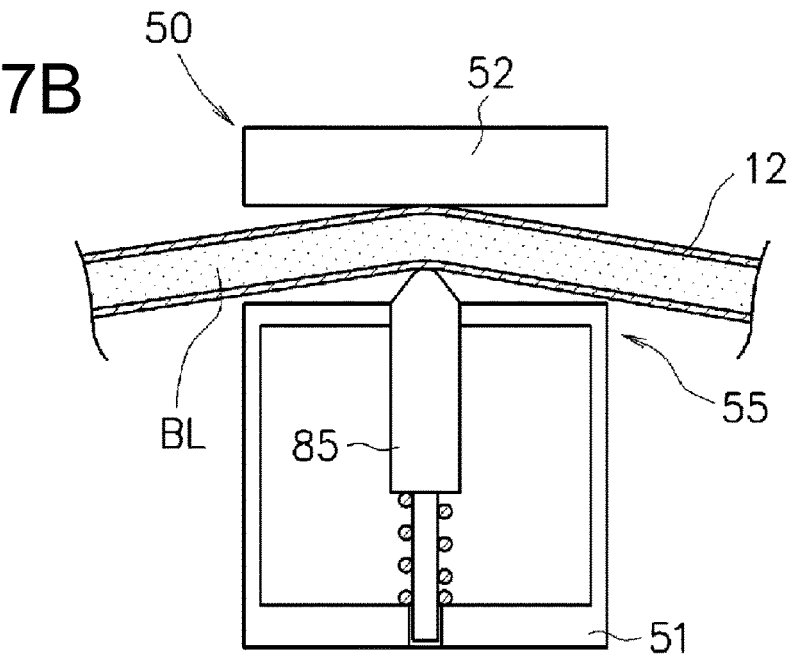

FIG. 7 illustrates abnormal clamping caused by insufficient locking of the lid portion 52. That is, in a case where the lid portion 52 is insufficiently locked as illustrated in FIG. 7(A) (including a case where the lid portion 52 is not locked), even if the control unit 100 outputs the blocking instruction TA, and the plunger 85 is moved to the lid portion 52 and presses the blood transfer tube 12, a pressing force applied to the blood transfer tube 12 is reduced such that the blood transfer tube 12 may not be blocked (i.e., pinching does not occur) as illustrated in FIG. 7(B) and blood BL may continue to flow.

Figure 8A:
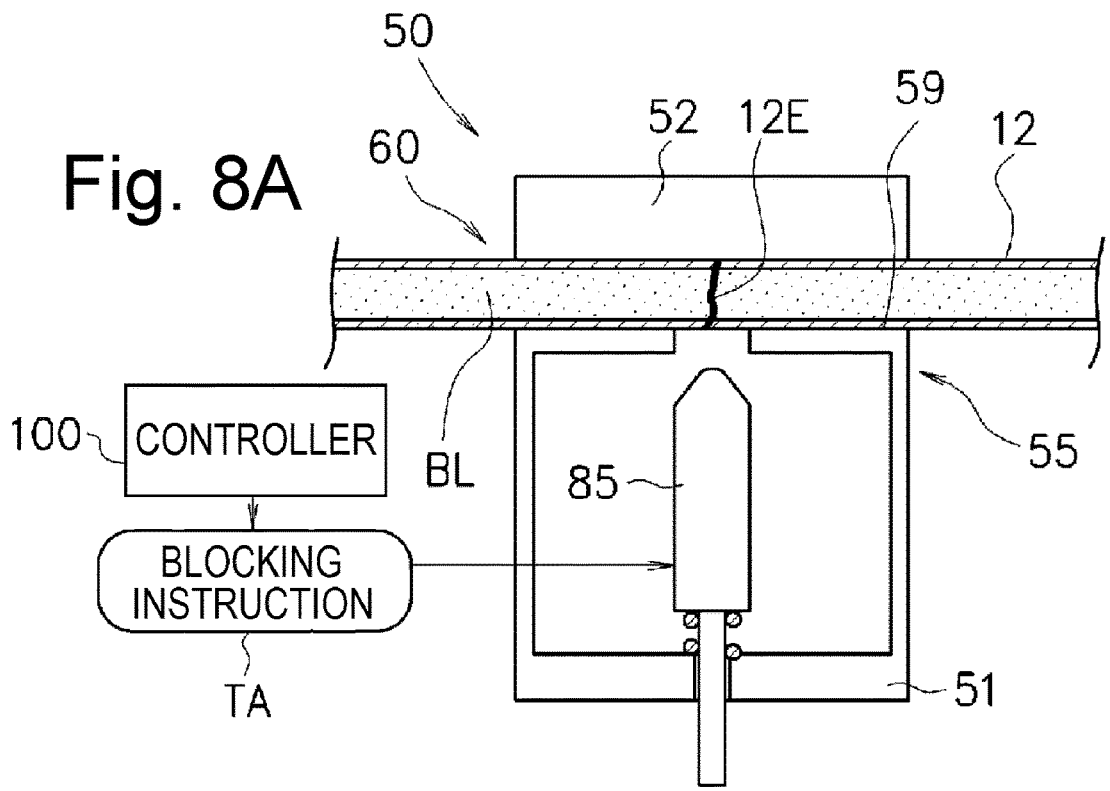
FIG. 8A and FIG. 8B are views illustrating abnormal clamping of a blood transfer tube in a case where the blood transfer tube has ruptured.
Figure 8B:
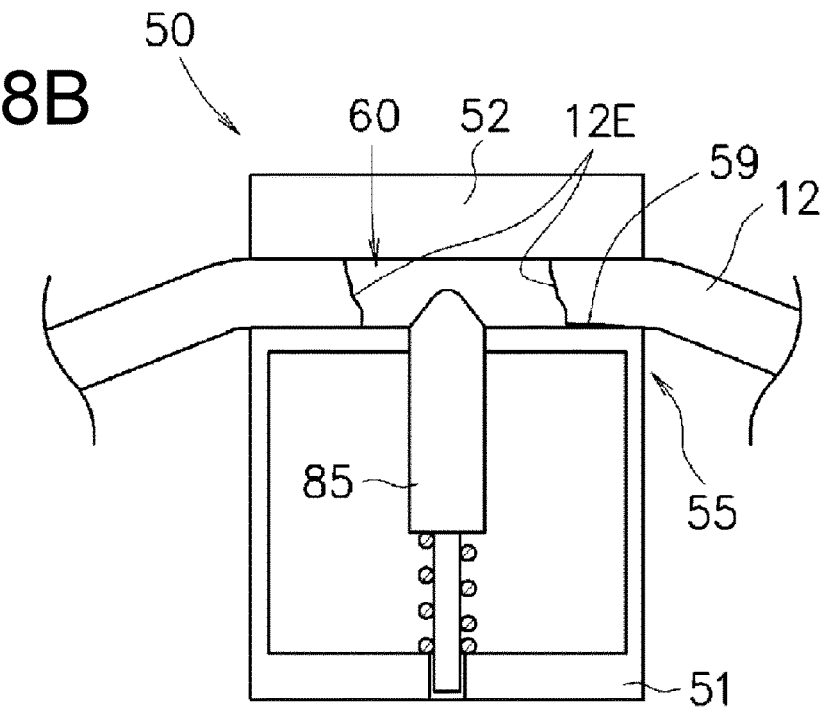

FIG. 8 illustrates abnormal clamping caused by a rupture of the blood transfer tube 12. That is, as illustrated in FIG. 8(A), in the tube clamp 50, the blood transfer tube 12 is mounted in the mounting space 60, and the lid portion 52 is reliably closed. In contrast, since the blood transfer tube 12 has a weak portion 12E, in a case where the plunger 85 receives the blocking instruction TA from the control unit 100, and presses the blood transfer tube 12, as illustrated in FIG. 8(B), the weak portion 12E of the blood transfer tube 12 has ruptured.

Figure 9A:
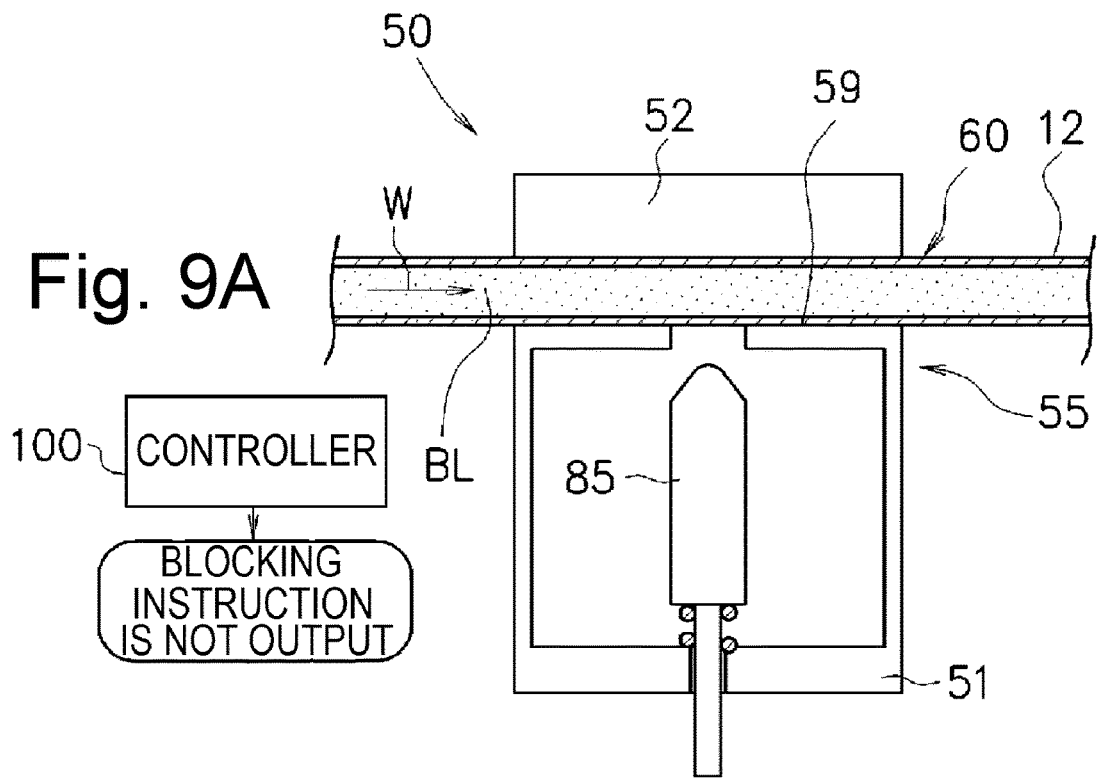
FIG. 9A and FIG. 9B are views illustrating a case in which a blood transfer tube is erroneously blocked, despite the fact that a control unit does not output a blocking instruction.
Figure 9B:
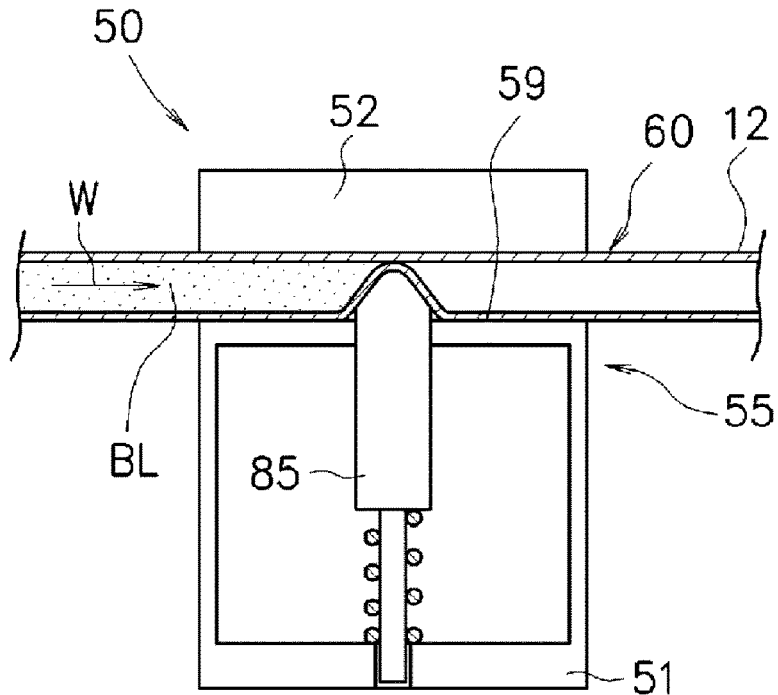

FIG. 9 illustrates an abnormally clamped state in which the blood transfer tube 12 is erroneously blocked, despite the fact that the control unit 100 does not output a blocking instruction. That is, in FIG. 9(A), the blood transfer tube 12 is mounted in the mounting space 60, and the lid portion 52 is closed. As illustrated in FIG. 9(B), the plunger 85 presses the blood transfer tube 12 despite the fact that the control unit 100 does not output a blocking instruction. In this state, an abnormal situation occurs in which the blood BL is shut off which is not intended to be shut off.

Figure 10A:
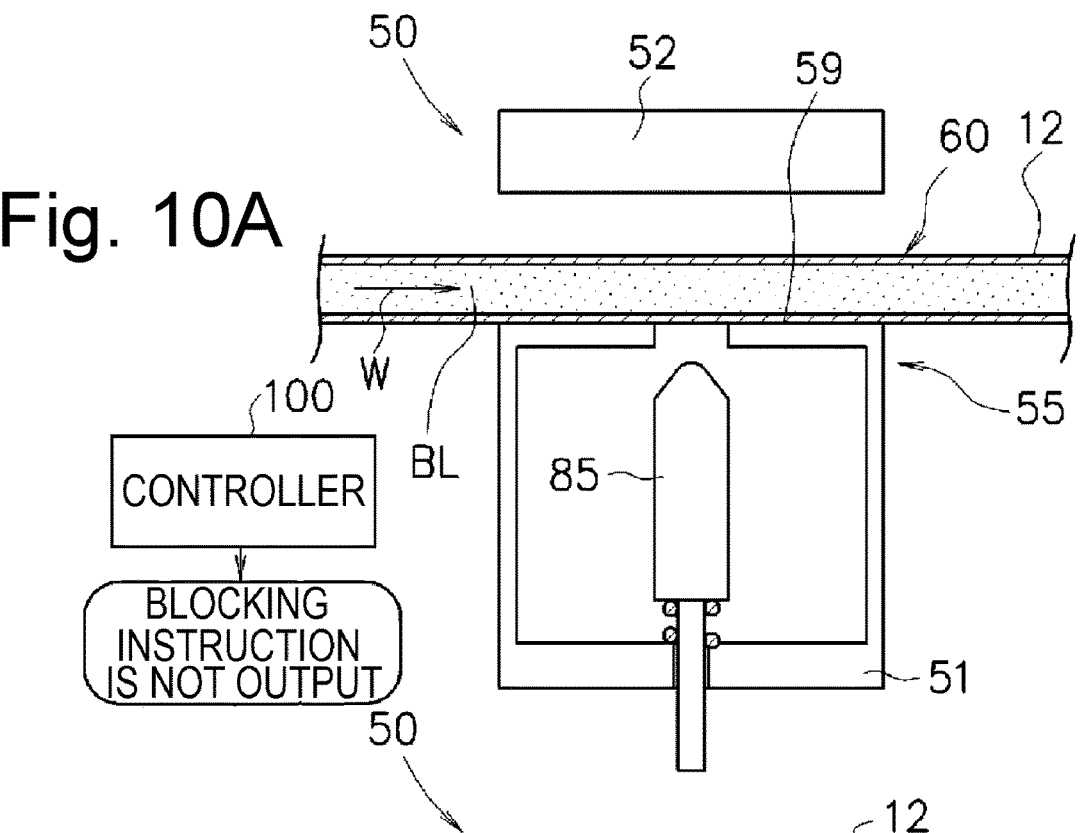
FIG. 10A and FIG. 10B are views illustrating an abnormality in which preparation for use of the tube clamp has not been completed.
Figure 10B:
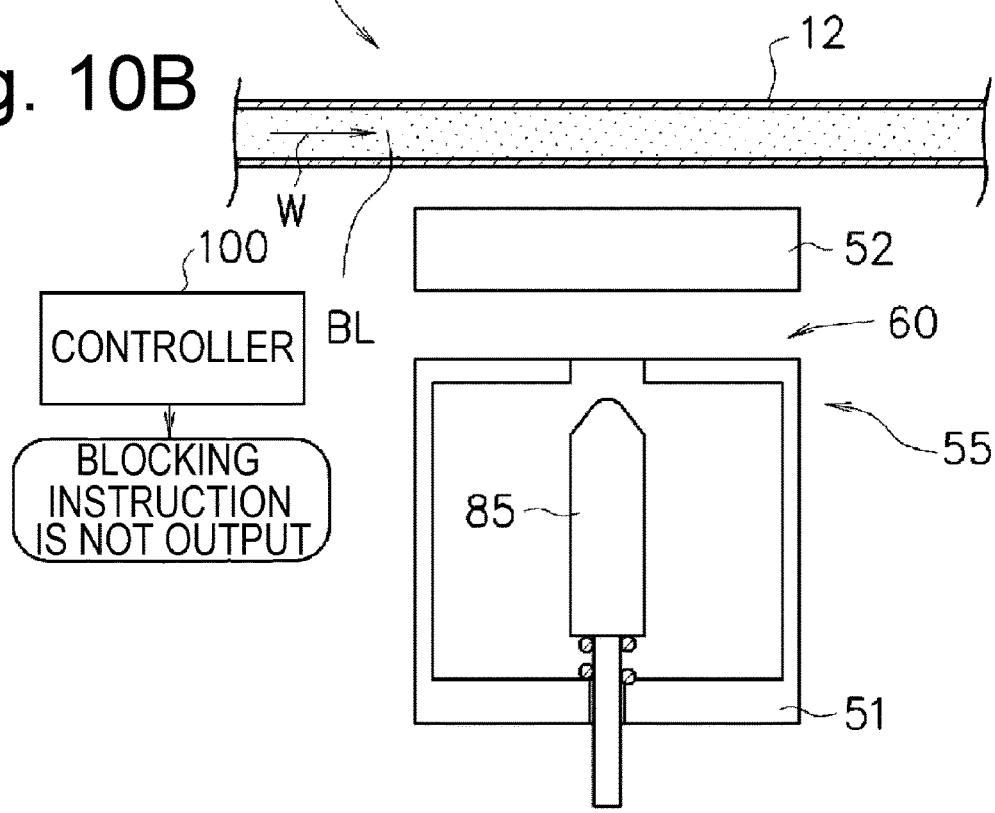

FIG. 10 illustrates an example of an abnormality in which preparation for use of the tube clamp 50 has not been completed. That is, as illustrated in FIG. 10(A), the lid portion 52 is open, and the blood transfer tube 12 is not fixed. As a result, even if the plunger 85 presses the blood transfer tube 12 in a case where blocking of the blood transfer tube 12 is required, a sufficient pressing force cannot be applied thereto, and preparation has not been completed such that the blood transfer tube 12 cannot be blocked. Similar to FIG. 10(A), in FIG. 10(B), since the blood transfer tube 12 is not mounted in the mounting space 60, preparation has not been completed such that the blood transfer tube 12 cannot be blocked whenever necessary.

In a case where there are such various abnormalities of clamping, the extracorporeal circulator 1 in the embodiment is capable of properly notifying a user of the abnormalities.

Figure 11:
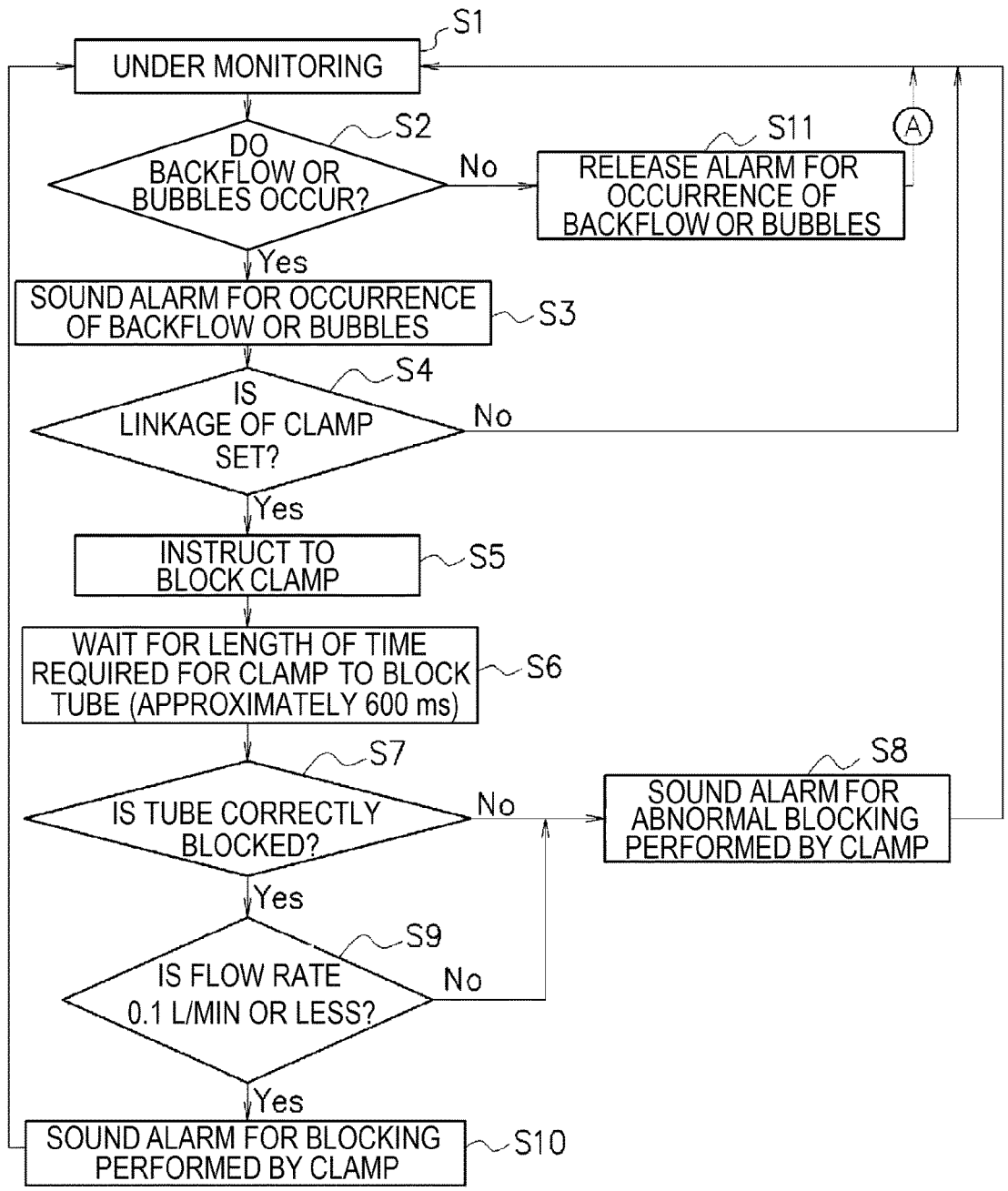
FIG. 11 is a flowchart illustrating a case in which mainly the control unit outputs a blocking instruction.

First, an example of an operation when a blocking instruction is output will be described with reference to FIG. 11 (refer to FIG. 1 for a reference sign assigned to each component below unless specified). FIG. 11 is a flowchart illustrating a case in which mainly a blocking instruction is output.

In Step S1 illustrated in FIG. 11, the extracorporeal circulator 1 monitors the occurrence of bubbles or the backflow of blood, and preparation for use of the extracorporeal circulator 1 is required as a prerequisite of monitoring. That is, preparations such as the fixing of the blood drainage tube 11 to the bubble flow rate detecting sensor 20, and the fixing of the blood transfer tube 12 to the tube clamp 50 are done. Catheter connection portions CN and CM for releasing air from the inside of the blood circuit 1R are connected to tubes which are separately prepared, and the blood circuit 1R is filled with a physiological salt solution. Thereafter, the blood drainage tube 11 is connected to the vein catheter 5, the blood transfer tube 12 is connected to the artery catheter 6, and a midway portion of the blood transfer tube 12 is clamped and blocked with forceps or the like. Thereafter, the rotational speed of the drive motor 4 is increased to a desired value, and then a blocked state is released by removing the forceps, and circulation of the physiological salt solution inside the circulation circuit 1R is started by further increasing the rotational speed of the drive motor 4.

In Step S1 illustrated in FIG. 11, the occurrence of bubbles and the backflow of blood are monitored. That is, the bubble flow rate detecting sensor 20 monitors the occurrence of bubbles or the backflow of blood in the blood circuit 1R. The bubble flow rate detecting sensor 20 transmits a detected result indicating existence or absence of bubbles, and a detected result indicating the value of a blood flow rate to the control unit 100.

As a result, in a case where the control unit 100 determines that there is no occurrence of bubbles or the backflow of blood (Step S2 in FIG. 11), the control unit 100 brings the alarm 200, which notifies a user of the occurrence of bubbles or the backflow of blood, into an alarm release state such that the alarm 200 is not sounded (Step S11 in FIG. 11), and continuously performs monitoring (Step S1 in FIG. 11).

On the other hand, in a case where, in Step S2 illustrated in FIG. 11, the control unit 100 determines that there is the occurrence of bubbles or the backflow of blood, the alarm 200, which notifies a user of the occurrence of bubbles or the backflow of blood, is sounded to warn the user (Step S3 in FIG. 11).

Subsequently, in Step S4 illustrated in FIG. 11, the control unit 100 confirms whether the linkage setting of the clamp is performed. The linkage setting of the clamp implies that the control unit 100 and the tube clamp 50 are properly prepared and interconnected so that they can be operated such that the blood transfer tube 12 is blocked in emergency situations.

In a case where, in Step S4, it is determined that the linkage setting of the clamp is not set, the control unit 100 returns to Step S1 in FIG. 11.

In contrast, in a case where it is determined that the linkage setting of the clamp is correctly set, the control unit 100 outputs a blocking instruction to the tube clamp 50 (Step S5 in FIG. 11). That is, the control unit 100 illustrated in FIG. 5(A) outputs the blocking instruction TA to the solenoid 89. The retracted state of the plunger 85 including the shaft portion 87 illustrated in FIG. 5(A) is released, as illustrated in FIG. 5(B), the plunger 85 presses the blood transfer tube 12 against the lid portion 52 via the force of the spring 86, and the blood transfer tube 12 is tightened and blocked with the plunger 85 and the lid portion 52.

Since a certain length of time (for example, 600 ms) is taken for the state of the plunger 85 to change from the retracted state illustrated in FIG. 5(A) to a closed state illustrated in FIG. 5(B), the control unit 100 wait at least for the movement time of the plunger 85 (Step S6 in FIG. 11).

Subsequently, in Step S7 illustrated in FIG. 11, it is determined whether the blood transfer tube is correctly blocked. The "correctly blocked state" implies a state in which the lid sensor 80 detects the closure of the lid portion 52 as illustrated in FIG. 6(B), the tube sensor 70 detects the mounting of the blood transfer tube 12 as illustrated in FIG. 4(B), and the plunger sensor 90 detects the movement of the plunger 85 to the lid portion 12 as illustrated in FIG. 5(B) (hereinafter, "detection of the three states" implies that the closure of the lid portion, the mounting of the tube, and the movement of the plunger 85 are detected by three sensors).

In a case where, in Step S7 illustrated in FIG. 11, the control unit 100 receives the tube setting state signal TS in FIG. 4(B), the closed state signal TR in FIG. 6(B), and the tube blocking signal TP in FIG. 5(B) as results of the detection of the three states, and determines that a normal blocked state has been achieved, the control unit 100 proceeds to Step S9 in FIG. 11, and it is attempted to confirm whether the bubble flow rate detecting sensor (flow rate detecting sensor) 20 substantially does not detect the blood flow rate. Not only the detection of the three state but also substantially no detection of the blood flow are confirmed based on the assumption that the sensors provided in the tube clamp 20 is out of order. If the three states are detected and if the blood flow rate is not substantially detected, a confirmation alarm is sounded to notify a user that the blood transfer tube is eventually correctly blocked (Step S10 in FIG. 11).

Figure 13A:
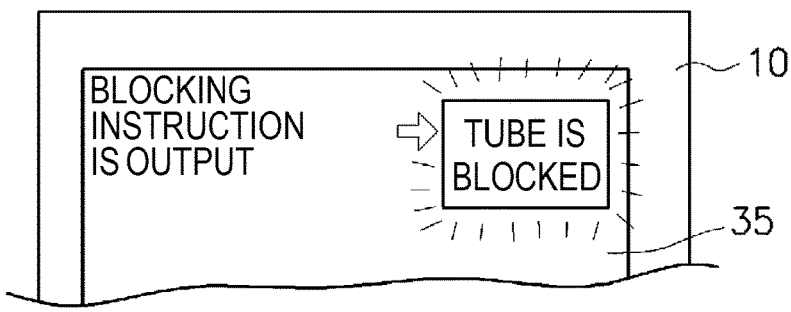
FIG. 13A, FIG. 13B, FIG. 13C, and FIG. 13D are views illustrating an example of a notification content that can be displayed on a display screen.

In addition, as illustrated in FIG. 13(A), the display screen 35 connected to the control unit 100 of the controller 10 displays a message indicating that the blocking instruction is output and a message indicating that the tube is blocked as intended, wherein the messages are displayed concurrently with the alarm being sounded in Step S10 illustrated in FIG. 11.

The "substantially no detection of the blood flow rate" implies that "there is no detection of a flow rate exceeding the flow rate of blood which still flows through the tube even if the tube is properly blocked". The flow rate is dependent on performance or disposition of the bubble flow rate detecting sensor 20. In the embodiment, in a case where a blood flow rate is 0.1 L/min or less, the control unit 100 determines that the blood transfer tube 12 is properly blocked. Preferably, a flow rate which is not substantially detected can be properly selected within the range of a blood flow rate of 0.1 L/min to 1.0 L/min.

In contrast, in a case where, in Step S7 illustrated in FIG. 11, any one of the three states is not detected by the clamp sensing means provided in the tube clamp 50, that is, in a case where the control unit 100 does not receive any one of the tube setting state signal TS in FIG. 4(B), the closed state signal TR in FIG. 6(B), and the tube blocking signal TP in FIG. 5(B), the control unit 100 detects that the tube is not normally blocked as intended, and then notifies a user that the blocking of the clamp is abnormal via the alarm 200 (Step S8 in FIG. 11). Examples of such a case include a case in which the lid portion 52 is insufficiently locked as illustrated in FIG. 7, a case in which the blood transfer tube 12 has ruptured as illustrated in FIG. 8, a case in which the plunger 85 is not moved due to damage to the spring 86 in FIG. 5, and the like.

In a case where the three states can be detected by the clamp sensing means, concurrently with a blood flow rate exceeding a predetermined flow rate (in the embodiment, 0.1 L/min) being detected in Step S9 illustrated in FIG. 11, the control unit 100 determines that the blocking of the clamp is abnormal, and notifies a user of the abnormality via the alarm 200 (Step S8 in FIG. 11).

Figure 13B:
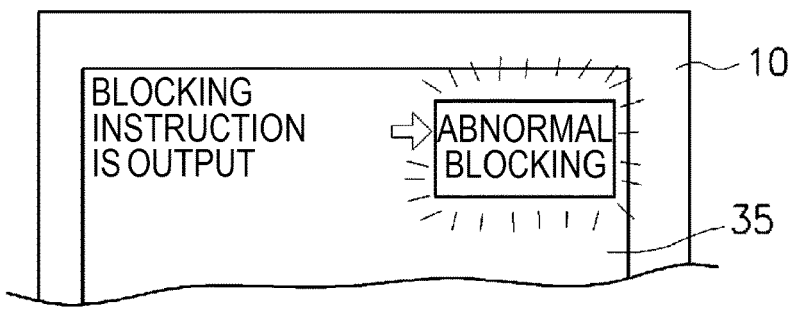

In this embodiment, an alarm sound in Step S8 illustrated in FIG. 11 can be a high-priority alarm, set to be the same as that in Step S10 illustrated in FIG. 11. A user can confirm the state of the tube via the display screen 35 of the controller 10, concurrently when the alarm is sounded. For example, as illustrated in FIG. 13(B), the display screen 35 displays a message indicating that a blocking instruction is output, and a message indicating that the tube is abnormally blocked. A user would suspect that bubbles could be transferred to a patient, and then quickly takes proper countermeasures.

Hereinafter, an example of an operation when a blocking instruction is not output by the controller will be described with reference to mainly FIG. 12 (refer to FIG. 1 for a reference sign assigned to each component below unless specified).

Figure 12:
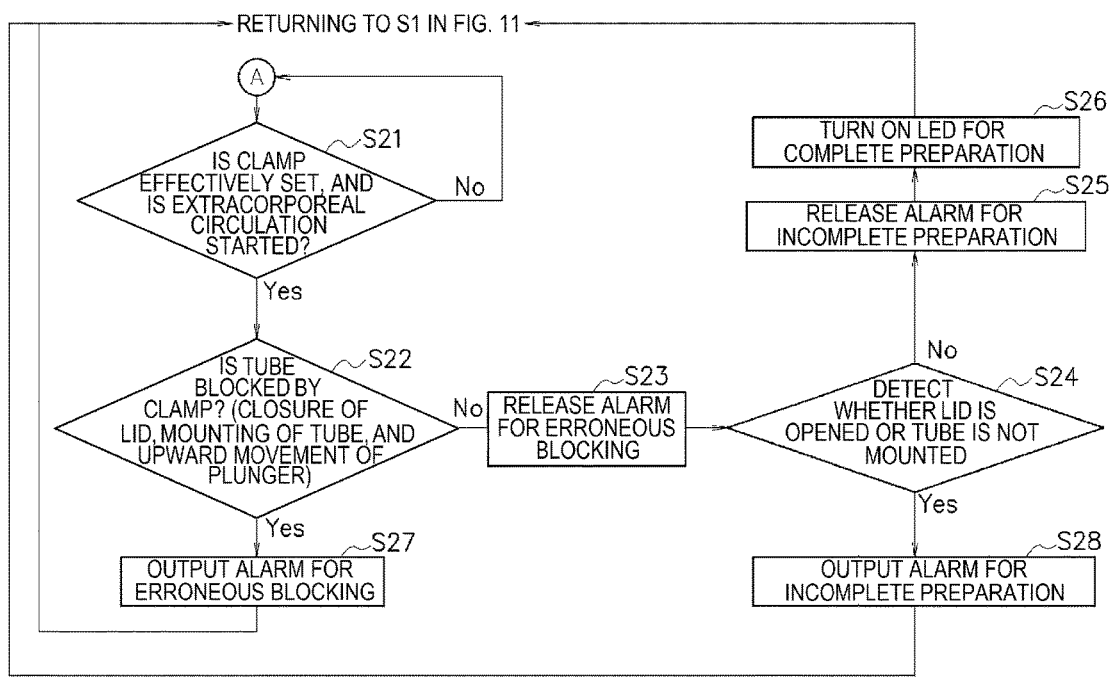
FIG. 12 is a flowchart illustrating a case in which the control unit does not output a blocking instruction.

FIG. 12 is a flowchart illustrating a case in which neither a backflow nor bubbles are detected, and the control unit does not output a blocking instruction. Step S21 in FIG. 12 is a step which is performed subsequent to Step S11 in FIG. 11. In a state where there is no blocking instruction, at first, the blood circuit 1R is set such that the tube clamp 50 is effectively used, and the control unit 100 determines whether the operation of the extracorporeal circulator 1 is started. Specifically, the control unit 100 of the controller 10 determines whether the linkage of the tube clamp 50 is set, and whether the rotational speed of the drive motor 4 is a desired rotational speed or more (changing depending on the state of a patient or the like, for example, 1250 rpm). In a case of a negative result, the control unit 100 does not proceed to the next step, and repeats determination in Step S21 illustrated in FIG. 11. The execution of Step S21 is to avoid the sounding of the alarm 200 in a case where extracorporeal circulation is at a preparation stage or the tube clamp 50 is not in use. Alternatively, Step S21 is not necessarily performed, and the control unit 100 can proceed to Step S22 in FIG. 12.

In contrast, in a case where the control unit 100 determines that the tube clamp 50 is set to be effectively used and the operation of the extracorporeal circulator 1 is started, the control unit 100 proceeds to Step S22 in FIG. 12, and even if there is no blocking instruction, the control unit 100 monitors whether the three states (the closure of the lid portion, the mounting of the tube, and the movement of the plunger) are detected.

In a case where the three states are detected despite the fact that there is no blocking instruction (that is, in a case where the state illustrated in FIG. 9(B) is reached), the alarm 200 (i.e., the notification means) notifies a user that the tube clamp 50 is erroneously blocked (Step S27 in FIG. 12).

Figure 13C:
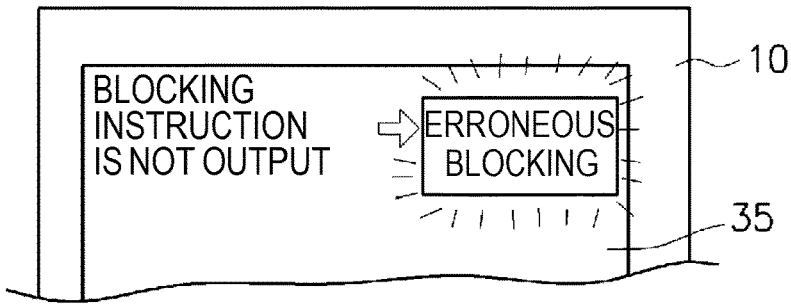

As illustrated in FIG. 13(C), the display screen 35 displays a message indicating that a blocking instruction is not output, and a message indicating that the tube is erroneously blocked, while an alarm is simultaneously sounded. As a result, a user can quickly take measures so as to eliminate a blocked state by lifting the operation lever 53 in FIG. 2 upwards in the R1 direction, or opening the lid portion 52.

In contrast, in a case where any one of the three states is not detected in Step S22 illustrated in FIG. 12, since the tube is not in a blocked state, the control unit 100 sets an alarm release state such that an alarm for erroneous blocking is not sounded (Step S23 in FIG. 12).

Subsequently, in a case where the lid sensor 80 illustrated in FIG. 6 detects that the lid portion 52 is open, or the tube sensor 70 illustrated in FIG. 4 detects that the blood transfer tube 12 is not mounted in the mounting space 60 (Step S24 in FIG. 12), the control unit 100 determines that the preparation of the tube clamp 50 has not been completed, and the alarm 200 is sounded to indicate that the preparation has not been completed (Step S28 in FIG. 12) as a lower priority alarm. An example of such a case is incomplete preparation illustrated in FIG. 10.

Figure 13D:
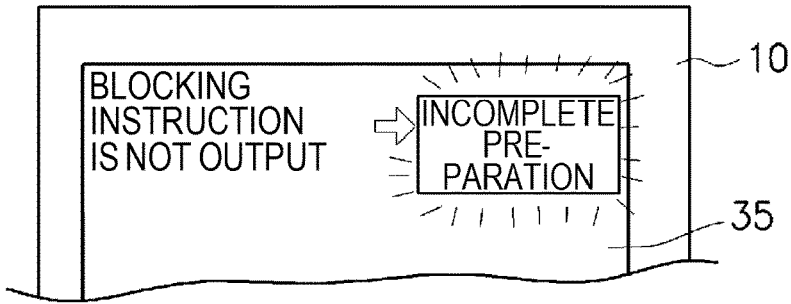

As illustrated in FIG. 13(D), the display screen 35 displays a message indicating that a blocking instruction is not output, and a message indicating that the preparation of the tube clamp has not been completed, concurrently when the alarm is sounded. In this case, a user can check the state of the tube clamp 50 while taking other possible emergencies into consideration.

In contrast, if, in Step S24 illustrated in FIG. 12, the lid sensor 80 detects that the lid portion 52 is closed and if the tube sensor 70 illustrated in FIG. 4 detects a mounting state in which the blood transfer tube 12 is mounted in the mounting space 60, in Step S22 illustrated in FIG. 12, it should be determined that the plunger is not moved to the lid portion (in other words, since the three states are not detected in Step S22 illustrated in FIG. 12, the lid portion is closed, and if the tube is mounted, the plunger cannot be moved). Therefore, as illustrated in FIG. 5(A), it means that the preparation for use of the tube clamp 50 has been completed. Accordingly, the control unit 100 proceeds to Step S25 in FIG. 12, and sets an alarm release state such that an alarm for incomplete preparation is not sounded (Step S25 in FIG. 12). Thereafter, the control unit 100 notifies a user that the preparation of the tube clamp 50 has been completed by instructing the display means (in the embodiment, a lamp) 75 of the tube clamp 50 illustrated in FIG. 3 to light up (Step S26 in FIG. 12), and then the control unit 100 returns to Step S1 illustrated in FIG. 11, and continuously performs monitoring.

The extracorporeal circulator 1 in the embodiment has the aforementioned configuration such that a user can properly recognize various abnormal situations of the tube clamp 50. The present invention is not limited to the embodiment, and modifications can be made to the embodiment in various forms insofar as the modifications do not depart from the claims.

The clamp sensing means in the embodiment is formed of the tube sensor 70, the lid sensor 80, and the plunger sensor 90; however, insofar the three states can be detected, the present invention is not limited to that configuration. For example, one tube/lid sensor can be configured to perform the functions of the tube sensor 70 and the lid sensor 80. The basic configuration of the tube/lid sensor is the same as that of the tube sensor 70 illustrated in FIG. 4. When the blood transfer tube 12 is placed into the mounting space 60, and the mounting space 60 is closed by the lid portion 50, the detection end portion 71 is eventually securely rotated in the F direction illustrated in FIG. 4, and the tube/lid sensor transmits a signal, which indicates that the tube is mounted and the lid portion is closed, to the control unit 100. Accordingly, it is possible to reduce a configuration component (the lid sensor 80) of the sensing means.

The tube clamp 50 in the embodiment is disposed on the blood transfer tube 12; however, the present invention is not limited to this disposition, and for example, may be disposed on a bypass circuit.

The monitoring of a blood flow rate is adopted as a preferable mode in Step S10 illustrated in FIG. 11; however, this monitoring is not a prerequisite.

A mechanical sensor, which is in mechanical contact with a tube, is used as the tube sensor 70; however, a contactless optical sensor may be used. In contrast, contactless optical sensors are used as the lid closing sensor 80 and the plunger sensor 90; however, mechanical sensors may be used.

In the illustrated embodiment, bubbles and a blood flow rate are simultaneously detected by one sensor; however, the present invention is not limited to this configuration, and bubbles and a blood flow rate may be separately detected. In this case, a sensor is not limited to an ultrasonic sensor.

What is claimed is:

1. An extracorporeal circulator that transfers blood out of a body of a patient and recirculates the blood, comprising:
   a tube carrying a flow of the blood outside the body of the patient;

a tube clamp that selectably blocks the tube in response to a blocking instruction, wherein the tube clamp includes:
- a body portion including a passageway in which the tube is mounted;
- a lid portion that encloses the passageway;
- a movable plunger that selectably presses the tube to block the blood flow; and
- a sensor assembly that detects a mounting state in which the tube is mounted in the passageway, a closed state in which the passageway is enclosed by the lid portion, and a movement state in which the plunger is moved;

a flow rate sensor that detects a blood flow rate in the tube; and a controller coupled to the plunger to provide the blocking instruction to selectably move the plunger, and coupled to the sensor assembly to detect the mounting, closed, and movement states and to generate respective alarms for abnormal states including a notification to a user in the event that the tube is not blocked at a time when the blocking instruction is being provided and the controller fails to detect any one of the closed state, the mounting state, or the movement state;

wherein the controller generates a respective notification to the user indicating that the tube clamp correctly blocks the tube when i) the blocking instruction is being provided, ii) the closed state, the mounting state, and the movement state are all detected, and iii) the flow rate sensor detects a blood flow rate below a threshold.

2. The extracorporeal circulator of claim 1 wherein the respective alarms for abnormal states further includes a notification to the user in the event that the tube is blocked at a time when the blocking instruction is not being provided and the controller detects the closed state, the mounting state, and the movement state.

3. The extracorporeal circulator of claim 1 wherein the controller generates a respective notification to the user in the event that preparation for use of the tube clamp has not been completed at a time when there is no blocking instruction and the controller does not detect either the closed state or the mounting state.

4. The extracorporeal circulator of claim 1 wherein the controller generates a respective notification to the user in the event that preparation for blocking the tube has been completed if the movement state is not detected and the closed state and the mounting state are detected.

5. An extracorporeal circulator that transfers blood out of a body of a patient and recirculates the blood, comprising:
a tube carrying a flow of the blood outside the body of the patient;
a tube clamp that selectably blocks the tube in response to a blocking instruction, wherein the tube clamp includes:
- a body portion including a passageway in which the tube is mounted;
- a lid portion that encloses the passageway;
- a movable plunger that selectably presses the tube to block the blood flow; and
- a sensor assembly that detects a mounting state in which the tube is mounted in the passageway, a closed state in which the passageway is enclosed by the lid portion, and a movement state in which the plunger is moved;

a flow rate sensor that detects a blood flow rate in the tube; and a controller coupled to the plunger to provide the blocking instruction to selectably move the plunger, and coupled to the sensor assembly to detect the mounting, closed, and movement states and to generate respective alarms for abnormal states including a notification to a user in the event that the tube is blocked at a time when the blocking instruction is not being provided and the controller detects the closed state, the mounting state, and the movement state;

wherein the controller generates a respective notification to the user indicating that the tube clamp correctly blocks the tube when i) the blocking instruction is being provided, ii) the closed state, the mounting state, and the movement state are all detected, and iii) the flow rate sensor detects a blood flow rate below a threshold.

6. The extracorporeal circulator of claim 5 wherein the controller generates a respective notification to the user in the event that preparation for use of the tube clamp has not been completed at a time when there is no blocking instruction and the controller does not detect either the closed state or the mounting state.

7. The extracorporeal circulator of claim 5 wherein the controller generates a respective notification to the user in the event that preparation for blocking the tube has been completed if the movement state is not detected and the closed state and the mounting state are detected.

8. An extracorporeal circulator that transfers blood out of a body of a patient and recirculates the blood, comprising:
a tube carrying a flow of the blood outside the body of the patient;
a tube clamp that selectably blocks the tube in response to a blocking instruction, wherein the tube clamp includes:
- a body portion including a passageway in which the tube is mounted;
- a lid portion that encloses the passageway;
- a movable plunger that selectably presses the tube to block the blood flow; and
- a sensor assembly that detects a mounting state in which the tube is mounted in the passageway, a closed state in which the passageway is enclosed by the lid portion, and a movement state in which the plunger is moved;

a flow rate sensor that detects a blood flow rate in the tube; and a controller coupled to the plunger to provide the blocking instruction to selectably move the plunger, and coupled to the sensor assembly to detect the mounting, closed, and movement states and to generate respective alarms for abnormal states including a notification to a user in the event that preparation for use of the tube clamp has not been completed at a time when there is no blocking instruction and the controller does not detect either the closed state or the mounting state;

wherein the controller generates a respective notification to the user indicating that the tube clamp correctly blocks the tube when i) the blocking instruction is being provided, ii) the closed state, the mounting state, and the movement state are all detected, and iii) the flow rate sensor detects a blood flow rate below a threshold.

* * * * *